United States Patent [19]

Lutz

[11] Patent Number: 4,713,325
[45] Date of Patent: Dec. 15, 1987

[54] HYBRIDOMAS PRODUCING MONOCLONAL ANTIBODIES SPECIFIC FOR FELV P27

[75] Inventor: Hans Lutz, Ruedlinger, Switzerland

[73] Assignee: The Regents of the University of California, Berkeley, Calif.

[21] Appl. No.: 842,749

[22] Filed: Mar. 21, 1986

Related U.S. Application Data

[63] Continuation of Ser. No. 503,643, Jun. 14, 1983, abandoned, which is a continuation of Ser. No. 219,603, Dec. 24, 1980, abandoned.

[51] Int. Cl.$^4$ ............... C12Q 1/70; G01N 33/53; G01N 33/577
[52] U.S. Cl. .................................... 435/5; 424/85; 424/86; 435/7; 435/68; 435/240.27; 435/172.2; 435/235; 436/548; 436/811; 935/103; 935/104; 935/105; 935/108; 935/110
[58] Field of Search ............... 435/7, 68, 240, 172.2, 435/235, 241.5; 424/12, 85, 86; 436/548, 811; 935/103-105, 108, 110; 530/387, 388

[56] References Cited

U.S. PATENT DOCUMENTS 4,196,265  4/1980  Koprowski et al. ............... 435/240
4,271,145  6/1981  Wands et al. ...................... 435/240

OTHER PUBLICATIONS

Lutz, et al., Detection of Feline Leukemia Virus Infection, *Feline Practice*, vol. 10, No. 4, 1980, pp. 13-23.
Lutz, et al, Humoral Immune Reactivity to Feline Leukemia Virus, *Biological Abs.*, 1980, vol. 71, p. 1195.
Stone et al., Topologual Mapping of Marine Leukemia Virus Proteins, *Virology*, vol. 100, 1980, pp. 370-381.
Voller et al., The Use of the Enzyme-Linked Immunosorbent Assay in The Serology of Viral and Parasitic Disease Scand, *J. Immunol.*, vol. 8, 1978, 125-129.
Köhler, G. and Milstein, C., *Nature*, vol. 256, 495-497, (1975).
Biological Abstracts, vol. 71(2), 11422, (1980).
Lostrom et al., *Virology*, vol. 98, 336-350, (1979).
Schetters, H., Infection and Immunity, vol. 29, 972-980, (1980).

*Primary Examiner*—Christine M. Nucker
*Attorney, Agent, or Firm*—Bertram I. Rowland

[57] ABSTRACT

Compositions and method are described for the detection of feline leukemia virus. Hybridomas are prepared producing monoclonal antibodies specific for at least one determinant site for the protein p27 of feline leukemia virus (FeLV). The antibodies are used in an enzyme immunoassay for determination of feline leukemia virus.

7 Claims, No Drawings

HYBRIDOMAS PRODUCING MONOCLONAL ANTIBODIES SPECIFIC FOR FELV P27

CROSS-REFERENCE TO RELATED APPLICATIONS

This application is a continuation of application Ser. No. 503,643, filed June 14, 1983, now abandoned, which is a continuation of application Ser. No. 219,603, filed Dec. 24, 1980, now abandoned, which disclosures are incorporated herein by reference.

BACKGROUND OF THE INVENTION

1. Field of the Invention

With the advent of being able to produce substantially homogeneous compositions of antibodies specific for a particular determinant site, improved approaches to assaying for a wide range of compounds of physiological interest were opened. There are many practical advantages to the use of hybridomas for production of antibodies for use in competitive protein binding assays. By using hybridomas, the antibodies can be produced in a laboratory environment, rather than requiring immunization of animals, which generally results in a heterogeneous gamma-globulin fraction whose properties vary with the number of prior immunogen injections. Furthermore, the antisera obtained from immunization is a heterogeneous mixture of antibody molecules having varying specificities and binding constants.

In many situations, the heterogeneous character of the antisera derived from immunization of mammals can lead to a relatively high percentage of erroneous results. The conventional antisera may include antibodies which recognize conventional components in serum, which may or may not be universally encountered. Thus, situations can arise where false positives are observed due to the binding of components of the antisera to components of the serum sample other than the analyte. Monoclonal antibodies offer an important opportunity to provide antibodies which are specific for one or more determinant sites of an analyte diagnostic for a particular disease state or other physiologic condition of interest.

2. Description of the Prior Art

Lutz, et al., Feline Practice 10, 13–23 (1980) and Lutz et al., "Feline Leukemia Virus", W. D. Hardy et al. (Eds), Elsevier, North-Holland, N.Y. (1980) described an enzyme immunoassay test for group specific antigens for Feline Leukemia Virus infection and for p27 protein in the serum of cats. See also, Lutz et al., Cancer Res. 40: 3642–3651, 1980, and references cited therein. U.S. Pat. Nos. 4,172,124 and 4,196,265 describe the preparation of monoclonal antibodies for tumors.

SUMMARY OF THE INVENTION

Methods and compositions are provided for a sensitive and accurate detection of feline leukemia virus employing monoclonal antibodies specific for at least one determinant site of the p27 protein of the FeLV virus. Hybridomas are produced employing conventional techniques and specific hybridomas selected for their specificity in binding to the p27 protein in contrast to other proteins encountered in cat serum.

DESCRIPTION OF THE SPECIFIC EMBODIMENTS

Monoclonal antibodies are produced which are specific for one or more determinant sites of the p27 protein of feline leukemia virus (FeLV). The monoclonal antibodies are produced in conventional ways by immunizing a vertebrate with the p27 protein, isolating the spleen from the immunized vertebrate, combining the immunized spleen cells with myeloma cells in the presence of polyethylene glycol and selecting for the desired hybridomas. Normally this selection process involves the use of HAT-medium, followed by the growth of stable single clones using a limiting dilution procedure, and then screening the supernatants for antibodies having the desired specificity. The clones producing the desired monoclonal antibodies are then isolated and repeatedly passaged to ensure the stability of the line and the homogeneity of the monoclonal antibody composition.

The use of antibodies in competitive protein binding assays is well established. Numerous competitive protein binding assays have been described in the scientific and patent literature and a large number are commercially available. In many of these assays, but not all, the antibodies may be modified by labeling. In other instances, the antigen or ligand, which is also the analyte, may be labeled. In addition, there are assays, where neither the ligand nor antibody is labeled.

The more common labels include radionuclides, such as $^3H$, $^{125}I$, $^{14}C$, $^{36}Cl$, $^{32}P$, etc.; enzymes, particularly hydrolases and oxidoreductases; fluorescers, particles, and enzyme substrates. Assaying involving unmodified analytes and antibodies include nephelometric assays and assays dependent upon Rf binding to the antigen-antibody complex. The assays employing the subject antibodies may be homogeneous or heterogeneous. In heterogeneous assays, the antibodies may be covalently or non-covalently bonded to a surface, which may be inert or adsorbent, where the surface may be a layer, particle, or film.

Immunoassays of interest which may use the monoclonal antibodies of the subject invention with advantage include U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

Of particular interest in those assays where the antibody is labeled, are monoclonal antibodies of the subject invention covalently conjugated to a radionuclide, an enzyme, particularly a hydrolase or oxidoreductase: glycosidases, dehydrogenases, and peroxidases; and fluorescers, particularly those having absorption maxima above 350 nm, more desirably above 400 nm.

In view of the wide diversity of competitive protein binding assays which can employ the monoclonal antibodies of the subject invention, there is no general description to cover all the procedures. Rather, reference should be made to the available literature for the particular procedures and conditions in preparing the reagents and performing the assay. In each instance, optimization of the assay will be required, but this can be readily achieved by conventional ways.

There will be some generalities, in view of the assays being dependent upon the forming of an antigen-antibody complex. For the most part, an aqueous buffered medium will be employed, at a pH in the range of about 5.5 to 10, more usually from about 6 to 9. A wide variety of buffers can be employed and other reagents will also be included, such as salt to enhance the ionic strength, proteins, particularly serum albumins, stabilizers, biocides, and non-ionic detergents. In any individual assay, one or more of these additives will be included in varying amounts.

So far as the protocols, where a labeled antigen is employed, usually the labeled antigen will not be added to the antibody prior to the addition of the sample suspected of containing the antigen. Temperatures will generally range from about 20° to 45° C., more usually from about 25° to 40° C. Times will vary widely depending upon the nature of the assay, generally being not less than about 0.1 min and not more than about 12 hrs.

As illustrative of the competitive protein binding assays, an assay known under the acronym ELISA will be described. See U.S. Pat. Nos. 3,791,932; 3,839,153; 3,850,752; 3,879,262 and 4,034,074.

In this particular mode, the method described by Wolters, et al., (1976) J. Clin. Path., 29, 873-879 was employed. The technique is referred to as the double-antibody solid phase assay. The assay involves binding antibodies specific for the analyte to a solid surface, either covalently or non-covalently. The significant factor of binding is that the antibodies remain bound to the surface during the course of the assay. After washing the surface to ensure the absence of weakly bound or unbound protein, the sample dissolved in an appropriate buffer is added to the bound antibodies and incubated for sufficient time to ensure the binding of the analyte to the bound antibodies. Addition of a non-ionic detergent e.g. fatty acid ester of polyoxyethylene or polyoxypropylene ensures the accessibility of the p27 protein to antibodies.

After washing to ensure the removal of all non-specifically bound protein from the surface-bound-antibodies, antibodies to the analyte conjugated to an enzyme, e.g. horseradish peroxidase, is added in an appropriate buffer and the assay mixture incubated again. After the appropriate incubation period, the bound enzyme conjugated antibody is washed free of any non-specifically bound protein and a substrate solution added to provide a detectible signal, normally light absorption, which can be correlated to the amount of enzyme bound to the surface. By employing standards having known amounts of the FeLV p27 protein, the observed absorption may be correlated with the concentration of the p27 protein in the sample.

EXPERIMENTAL

The antigen was prepared as described by Lutz et al., (1980) Cancer Res. supra, and purified by SDS-polyacrylamide gel electrophoresis of $FeLV_{ABC}$ p27. The gel region containing p27 was cut from the gel and the gel homogenized with a Potter homogenizer. BALB/C mice were injected with gel containing 25 µg of p27. Basic immunization in the presence of complete Freunds adjuvant was intraperitoneally. The booster injections were applied subcutaneously. The immunization took place over six months in order to induce antibodies of high affinity to p27. The immune response of the mice was monitored by an ELISA procedure. (Lutz et al., Cancer Res. (1980), supra).

Spleens were removed from the immunized mice and the immunized spleen cells fused with myeloma cells SP 2/0 (Schulman et al., Nature (1978) 276: 269-270) in the presence of polyethylene glycol 6000 in accordance with the procedure described in Fazekas et al., J. Immuno. Methods (1980), 35: 1-21. The resulting hybrids were selected in 500 individual wells in HAT-medium as described in Fazekas, supra. Stable single clones were obtained by the limited dilution procedure described in Oi and Herzenberg: Immunoglobulin-Producing Hybrid Cell Lines. In Selected Methods in Cellular Immunology. Mishel B., Shiigi S. M. (eds), N. H. Freeman and Co., San Francisco, p. 351-372, 1980. Each of the cell culture supernatants were tested for antibody activity by the ELISA technique using p27 purified by SDS-polyacrylamide gel electrophoresis. Three of the monoclonal cell lines whose supernatants were shown to be positive for anti p27 monoclonal antibody were injected into BALB/C mice that were previously primed with 2,6,10,14-tetramethylpentadecane. The ascitic fluid was isolated and the monoclonal IgG was precipitated with 40% ammonium sulfate.

All of the three independently derived monoclonal antibodies showed the following specificity:

TABLE I

| Virus used for testing | Reactivity |
|---|---|
| $FeLV_{ABC}$ | +++ |
| $FeLV_A$ | +++ |
| $FeLV_B$ | +++ |
| $FeLV_C$ | +++ |
| $FeLV_{AB}$ | +++ |
| RD114 | — |
| MuLV (AKR-strain) | — |

An ELISA procedure described below was employed to test the specificity of the antibodies. A(−) indicates there was no indication of any substrate turnover. A (+++) indicates that the substrate was exhausted in five minutes, when the reading was taken. The volume of substrate employed was 100 µl and the reaction was terminated by addition of 100 µl 0.1M HF adjusted to pH3.3 with NaOH. The fact that the antibodies were specific for the various strains of FeLV but did not bind to the closely related MuLV is indicative of the high degree of specificity of the subject antibodies. One of the antibodies has been deposited at the ATCC on Dec. 23, 1980, with designation number HB Harry Boyer 8049, for patent purposes.

One of the three antibodies was tested with different FeLV proteins, showing strong specificity to p27 prepared by SDS-gel electrophoresis and p27 prepared conventionally by column chromatography. A conjugate of anti p27 monoclonal antibody with horseradish peroxidase was prepared in accordance with the procedure described by Wilson and Nakana: In: Immunofluorescence and Related Staining Techniques, Knapp W, et al. (eds). Elsevier/North Holland p.217, 1978. To 4 mg HRP in 1 ml $H_2O$ was added 0.1 ml freshly prepared 0.1M aqueous $NaIO_4$ and the mixture stirred for 20 min at 20° C. After dialyzing the above solution overnight with 1 mM NaOAc, pH4.4 at 4° C., the pH of the residue was raised to 9.5 by adding 10 µl 0.2M $Na_2CO_3$, followed immediately by the addition of 8 mg of monoclonal antibody in 1 ml 10 mM $Na_2CO_3$, pH 9.5. After stirring for 2 hrs at rt, 0.1 ml of freshly prepared $NaBH_4$ (4mg/ml) was added, the mixture stirred for 2 hrs at 4° C. and then chromatographed on a 35×2.5 cm Sephacryl S-200 column with PBS. Two ml fractions were collected and checked for the presence of the conjugate, with about 60% of the eluent being combined as showing the presence of conjugate. This conjugate was used in an ELISA assay for the detection of p27 in the serum of cats as described in Lutz et al, (1980), supra. This assay is generally described by Wolters, et al., supra.

In the assay, Gilford EIA-50 cuvette strips were coated with 5 μg IgG/well in 0.1M sodium bicarbonate, pH9.6, by incubating the solution and the cuvette strips for 3 hrs at 37° C. the cuvette strips were then stored at 4° C. until used. Immediately before use, the cuvette strips were washed four times with 0.15M NaCl, 0.05% Tween 20. To the walls were then added 50 μof serum together with 50 μl of Buffer A (0.15M NaCl, 1 mM EDTA, 0.05M Tris-HCl, 0.1% BSA,) containing 0.2% Tween 20 and the solution incubated for 1 hr at 37° C. (At a final concentration of 0.1% Tween 20, the envelope is stripped from the virus and p27 becomes accessible to antibodies). After washing, as described above, 1 μg anti-FeLV p27 IgG conjugated to horseradish peroxidase as described above in 100 μl Buffer A containing 0.05% Tween 20 was added to the well and incubated for 1 hr at 37° C. Following a third washing as indicated above, 300 μl of substrate was added and the absorbance of the reaction product was determined after 10 min at 405 nm. (The substrate is 0.2 mM 2,2-azino-di-(3-ethylbenzthiazolidine) sulfonate and 2 mM $H_2O_2$ in 50 mM citric acid neutralized to pH4 with 1N NaOH). Cats known to be infected with FeLV were clearly shown to be positive for p27 in the subject assay.

In accordance with the subject invention, an improved accurate method is provided for detecting the presence of FeLV in serum, where errors due to erroneous or non-specific binding by antibodies is substantially eliminated. Furthermore, the monoclonal antibodies provide for a uniform product with which substantial clinical experience can be achieved. This may be contrasted with antisera from immunization which may vary from animal to animal and bleed to bleed.

Although the foregoing invention has been described in some detail by way of illustration and example for purposes of clarity of understanding, it will be obvious that certain changes and modifications may be practiced within the scope of the appended claims.

What is claimed is:

1. Murine hybridoma cells producing and secreting monoclonal antibodies specific for a determinant site of the p27 protein of feline leukemia virus, and capable of distinguishing the A, B, C, AB, and ABC strains of FeLV from murine leukemia virus (AKR strain).

2. Murine hybridoma cells having A.T.C.C. Designation No. HB 8049.

3. In a method for determining the presence of feline leukemia virus by detecting a protein diagnostic of feline leukemia virus by means of an immunoassay,
   which comprises combining a sample containing feline leukemia virus with labeled or unlabeled antibodies, whereby the binding of antibodies to a component of feline leukemia virus results in a detectable signal, and determining said detectable signal,
   the improvement which comprises employing monoclonal antibodies specific for a determinant site of the p27 protein of feline leukemia virus, and capable of distinguishing the A, B, C, AB, and ABC strains of FeLV from murine leukemia virus (AKR strain).

4. A method according to claim 3, wherein said method is an enzyme immunoassay.

5. A method according to claim 4, wherein said enzyme immunoassay is an enzyme linked immunosorbent assay.

6. A method according to claim 3, 4 or 5, wherein said monoclonal antibodies are murine monoclonal antibodies.

7. In a method for determining the presence of feline leukemia virus by detecting a protein diagnostic of feline leukemia virus by means of an immunoassay,
   which comprises combining a sample containing feline leukemia virus with labeled or unlabeled antibodies, whereby the binding of antibodies to a component of feline leukemia results in a detectable signal, and determining said detectable signal,
   the improvement which comprises employing monoclonal antibodies are produced by murine hybridoma cell having A.T.C.C. Designation No. HB 8409.

* * * * *